United States Patent
Ludescher et al.

[11] Patent Number: 5,861,508
[45] Date of Patent: Jan. 19, 1999

[54] PURIFICATION OF A CEPHALOSPORIN SALT

[75] Inventors: Johannes Ludescher, Breitenbach; Rainer Pucher, Mariastein; Siegfried Wolf, Brixlegg, all of Austria

[73] Assignee: Biochemie Gesellschaft m.b.H., Kundl, Austria

[21] Appl. No.: 842,919

[22] Filed: Apr. 18, 1997

Related U.S. Application Data

[62] Division of Ser. No. 490,371, Jun. 14, 1995, Pat. No. 5,659,030.

[30] Foreign Application Priority Data

Jun. 14, 1994 [AT] Austria ................................. 1181/94

[51] Int. Cl.$^6$ .................................................. C07D 501/34
[52] U.S. Cl. ..................................................... 540/222
[58] Field of Search ............................ 540/222; 514/202

[56] References Cited

U.S. PATENT DOCUMENTS 5,409,918  4/1995  Friedhelm et al. ...................... 540/222

FOREIGN PATENT DOCUMENTS

0484966A2  5/1992  European Pat. Off. .
05230068A  9/1993  Japan .

OTHER PUBLICATIONS

Chem. Abstract 120:244446n vol. 120, 1994.
Journal of Pharmaceutical Sciences vol. 83, No. 10, Oct. 1994, 1500–1507 Ishihama et al.
The Journal of Antibiotics vol. 47 No. 12, 1507–1525 (Dec. 1994).
33rd Interscience Conference on Antimicrobial Agents and Chemotherpy New Orleans, Louisiana Oct. 19, 1993— Abstracts No. 893–896 Asada et al.

*Primary Examiner*—John M. Ford
*Attorney, Agent, or Firm*—George R. Dohmann

[57] ABSTRACT

A p-toluenesulphonic acid salt of 7-[2-(2-aminothiazol-4-yl)-2-(Z)-hydroximino-acetamido]-3-N,N-dimethyl carbamoyloxymethyl-3-cephem-4-carboxylic acid (isopropoxycarbonyloxy)ethylester, e.g. of formula

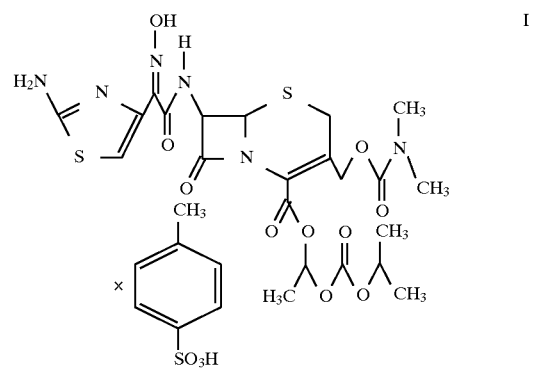

its use in the production of other salts and a pharmaceutical composition containing it.

5 Claims, No Drawings

PURIFICATION OF A CEPHALOSPORIN SALT

This is a division of application Ser. No. 08/490,371, filed Jun. 14, 1995 now U.S. Pat. No. 5,659,030.

This invention relates to cepholosporin salts. It provides in one aspect a p-toluene-sulphonic acid salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)-ethylester (hereinafter "compounds of the invention"), e.g. a compound of formula

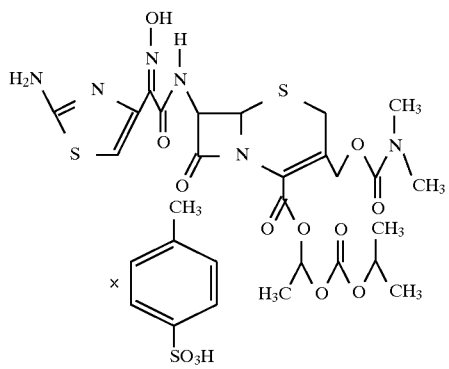

which may be crystalline.

This compound is a new highly active cephalosporin. Its active metabolite is 7-[2-(2-aminothiazol-4-yl)-2-(Z)-hydroximinoacetamido]-3-N,N-dimethylcarbamoyloxymethyl-3-cephem-4-carboxylic acid.

7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester and its active metabolite are described for example in EPA 484 966 and known from the 33rd Interscience Conference on Antimicrobial Agents and Chemotherapy, New Orleans, Abstracts No. 894, 895, 896 as the compounds E 1101 (ester) and E 1100 (free acid).

The compounds of the invention exhibit pharmacological activity and are, therefore, useful as pharmaceuticals. In particular, the compounds of the invention show the same activity for the same indications and may be administered in the same mode and in in the same doses as the above-mentioned prior art compounds.

In another aspect, the invention relates therefor to a pharmaceutical composition containing as an active ingredient a a p-toluene-sulphonic acid salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)-ethylester.

E 1101 is a hygroscopic, easily electrostatically chargeable compound and thus difficult to handle and to store. E 1101 as the hydrochloride salt has additionally a strong tendency to bind organic residual solvents. Furthermore, the hydrochloride salt is amorphous, which makes its precipitation and isolation extremely difficult. When isolating amorphous compounds, the possibility of including a purification step, as is offered, for example, when isolating the same compound in the crystalline state, is moreover impossible or only feasible to a slight extent.

Now, surprisingly a p-toluene sulphonic acid salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester was found which is unexpectedly crystalline, easy to handle, not hygroscopic and may be free from solvents. This novel salt thus eliminates the disadvantages of the corresponding amorphous hydrochloric acid salt.

In another aspect, the invention provides a process for the production of a compound of the invention, as defined above, by mixing the free base of a compound of the invention, or an acid-unstable O-hydroxylamine derivative therof, with p-toluenesulphonic acid.

This process may be carried out in various ways:

7-[2-(2-aminothiazol-4-yl)-2-(Z)-hydroximinoacetamido]-3-N,N-dimethylcarbamoyloxymethyl-3-cephem4-carboxylic acid (isopropoxycarbonyloxy)ethylester in free base form may be, for example, dissolved or suspended in a solvent or solvent mixture, and mixed with a p-toluenesulphonic acid hydrate, particularly the monohydrate or p-toluenesulphonic acid, mixed with a little water. A compound of the invention crystallises. Suitable solvents include esters, such as ($C_{1-4}$) acetic acid alkyl esters (straight chained or branched), for example ethyl- propyl- or butyl acetate, with or without the presence of a cosolvent. Suitable cosolvents include ($C_{1-4}$) alcohols, for example isopropanol or ethanol. The free base may also be dissolved in concentrated form in a solvent in which the compound is readily soluble, for example in dichloromethane, and then converted into a compound of the invention by adding p-toluenesulphonic acid hydrate or p-toluenesulphonic acid, mixed with a little water, and for example a ($C_{1-4}$)acetic acid alkyl ester.

A compound of the invention may, for example, also be produced, starting with an acid-unstable O-hydroxylamine derivative of 7-[2-(2-aminothiazol-4-yl)-2-(Z)-hydroximinoacetamido]-3-N,N-dimethylcarbamoyloxymethyl-3-cephem4-carboxylic acid (isopropoxycarbonyloxy)ethylester, such as 7-[2-(2-aminothiazol-4-yl)-2-(Z)-acetoxyiminoacetamido]-3-N,N-dimethylcarbamoyloxymethyl-3-cephem-4-carboxylic acid (isopropoxycarbonyloxy)ethylester or 7-[2-(2-aminothiazol-4-yl)-2-(Z)-tritylhydroximinoacetamido]-3-N,N-dimethylcarbamoyloxymethyl-3-cephem-4-carboxylic acid (isopropoxycarbonyloxy)ethylester and adding p-toluenesulphonic acid hydrate or p-toluenesulphonic acid, mixed with a little water. Deprotection of the hydroxyimino group and crystallisation of the compound of formula I may occur simultanously. Suitable solvents include the solvents mentioned above.

It was surprisingly found that a compound of the invention crystallizes in a highly pure form even from acylation solutions, containing E 1101, the corresponding cephalosporin nucleus as starting material and the 7-acylamino side chain which is protected on the oxygen atom by an acid-unstable protecting group, when adding p-toluenesulphonic acid hydrate or p-toluenesulphonic acid, mixed with a little water.

Hygroscopicity and residual solvent content of the hydrochloric acid salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester and the p-toluenesulphonic acid salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester, both compounds precipitated from the solvent system isopropyl acetate/isopropanol, are reproduced in Table 1:

TABLE 1

| E1101 | water content (starting value) | water content after 7 days in 75% atmospheric moisture at 25° C. | residual solvent isopropyl acetate | residual solvent isopropanol |
|---|---|---|---|---|
| hydrochloride | 1.7% | 4.3% | 1.5% | 0.05% |
| p-toluene-sulphonate | 0.4% | 0.6% | 0.1% | 0.06% |

From Table 1 may be seen that the p-toluenesulphonate is much less hygroscopic and contains much less residual solvent than the corresponding hydrochloride, both salts precipitated and treated under the same conditions.

The crystalline p-toluenesulphonic acid salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester shows the X-ray spectrum of Table 2. This X-ray spectrum was produced using following photographic conditions:

Apparatus: Siemens X-ray diffractometer D-500

Apparatus parameters: tube: Cu, Kβ-filtering: nickel excitation voltage: 40 kV, X-ray current: 30 mA wave length: CuKα$_{1+2}$=1.54060 Å (resp. 1.54443 Å) step size: 0.01 steps, measurement time: 5 seconds, temperature 20° C., range measured: 2° to 60°, 2 Θ.

Internal standard: NBS silicon SRM 640a

TABLE 2

| Reflex No. | d-value (Å) | I-value (rel.) |
|---|---|---|
| 1 | 28.247 | 100 |
| 2 | 14.089 | 2 |
| 3 | 9.473 | 25 |
| 4 | 6.821 | 3 |
| 5 | 6.500 | 6 |
| 6 | 6.395 | 4 |
| 7 | 5.726 | 4 |
| 8 | 5.521 | 7 |
| 9 | 5.384 | 6 |
| 10 | 5.014 | 16 |
| 11 | 4.942 | 18 |
| 12 | 4.683 | 5 |
| 13 | 4.407 | 6 |
| 14 | 4.255 | 9 |
| 15 | 3.994 | 13 |
| 16 | 3.863 | 9 |
| 17 | 3.718 | 2 |
| 18 | 3.622 | 1 |
| 19 | 3.488 | 7 |
| 20 | 3.320 | 5 |
| 21 | 3.258 | 2 |
| 22 | 2.989 | 1 |
| 23 | 2.341 | 1 |

A crystalline p-toluene-sulphonic acid salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester having at least the following d-values (Å) in the X-ray data: 28.247; 9.473; 5.014; 4.942; 3.994; also forms part of the invention.

In another aspect, the invention provides the use of a p-toluene-sulphonic acid salt of 7-[2-(2-aminothiazol-4-yl) 2-(Z)-hydroximinoacetamido]-3-N,N-dimethylcarbamoyloxymethyl-3-cephem-4-carboxylic acid (isopropoxycarbonyloxy)ethylester in the production of a different salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester, for example in the production of the hydrochloric acid salt.

In a further aspect the invention provides a process for the preparation of a salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester which comprises converting a p-toluene-sulphonic acid salt of 7-[2-(2-aminothiazol-4-yl)-2-(Z)-hydroximinoacetamido]-3-N,N-dimethylcarbamoyloxymethyl-3-cephem-carboxylic acid (isopropoxycarbonyloxy)ethylester into a different salt with an appropriate salt forming agent.

A process for the production of different salts starting from a compound of the invention may be carried out in accordance with methods known per se, for example by reacting a compound of the invention to form the free base, and reacting this free base with a desired salt forming agent, for example with an acid, such as hydrochloric acid.

The salts thus obtained may have a substantially lower content of by-products.

In the following examples all temperatures are given in degrees celsius.

EXAMPLE 1 p-toluenesulphonic acid salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester 7 g of 7-[2-(2-aminothiazol-4-yl)-2-(Z)-hydroxininoacetamido]-3-N,N-dimethylcarbamoyloxymethyl-3-cephem-4-carboxylic acid (isopropoxycarbonyloxy)ethylester are introduced into a mixture of 11.7 ml of isopropyl acetate and 2.3 ml of isopropanol. 2.7 g of p-toluenesulphonic acid monohydrate are added to the suspension and stirred until a solution is obtained. 11.7 ml of isopropyl acetate are added and stirring is stopped. The p-toluenesulphonic acid salt of 7-[2-(2-aminothiazol-4-yl)-2-(Z)-hydroximinoacetamido]-3-N,N-dimethylcarbamoyloxymethyl-3-cephem4-carboxylic acid (isopropoxycarbonyloxy)ethylester crystallizes. The crystal block is stirred for ca. 10 minutes and slowly mixed with 117 ml of isopropyl acetate. The crystal suspension is stirred for another hour whilst cooling with ice, and left over night in a refrigerator.

The crystals are isolated through a suction filter, washed with a little isopropyl acetate and dried for 3 hours in a vacuum at 40°.

$^1$HNMR (dmso d$_6$) (ppm): 12.37 (1H,s, OH); 9.77-9.76 (1H,dx2, J=8Hz, CONH); 9.15 (2H,b,NH$_2$); 7.52 (2H, d, J=5 Hz, ArH); 7.14 (2H, d, J=5Hz, ArH); 6.88 (1H, s, 5'''); 6.87-6.80 (1H, qx2, J=5Hz, 2'); 5.87-5.84 (1H, ddx2, J=8.5Hz, 7); 5.42-5.21 (1H, dx2, J=5Hz, 6); 4.39-4.38 (1H,dx2, J=13Hz, 1"Ha); 4.79 (1H, sep, J=6Hz, 4'); 4.69-4.67 (1H, dx2, J=13Hz, 1"Hb); 3.72, 3.70 (1H, dx2, J=18Hz, 4 Ha) 3.59, 3.58 (1H, dx2, J=18Hz, 4 Hb); 2.83-2.81 (6H, sx2, 3"); 2.29 (3H, s); 1.49 (3H, d, J=5Hz, 2'CH$_3$); 1.23-1.22 (6H, dx2, J=6Hz, 5').

Stoichometry of the tosylate: Theory: 22.28%; found by HPLC: 22.3%.

Melting point (uncorrected): Turns brown starting at 140°; decomposition starting at 185°.

EXAMPLE 2 p-toluenesulphonic acid salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester 48.6 ml of N,O-bistrimethylsilyl acetamide are added dropwise, whilst cooling with ice, to 42.2 g of the hydrochloric acid salt of 7-amino-3-N,N-dimethylcarbamoyloxymethyl-3-cephm4-carboxylic acid (isopropoxycarbonyloxy)ethylester in 420 ml of dichloromethane. 28.2 g of 2-(2-aminothiazol4-yl)-2-(Z)-acetoxyiminoacetic acid chloride hydrochloride are added to the solution in portions over the course of 20 minutes, whilst stirring and cooling with ice, and stirring continues for 45 minutes whilst cooling with ice. The acylation mixture is subsequently poured onto 250 ml of saturated NaHCO$_3$ solution and the pH value is adjusted to 7.5 with further NaHCO$_3$ solution. The phases are separated, the water phase is washed with 105 ml of dichloromethane, the dichloromethane phases are combined and washed with 250 ml of water. 34.2 g of p-toluenesulphonic acid monohydrate are added, and the resultant solution is stirred for 85 minutes. 300 ml of water are added, the phases are separated, the water phase is washed with 100 ml of dichloromethane, and the combined dichloromethane phases are washed with 200 ml of water. The dichloromethane phase is dried over Na$_2$SO$_4$ and concentrated by evaporation in a vacuum at a bath temperature of 30°. The residue of evaporation is dissolved in a mixture of 110 ml of dichloromethane and 1.7 ml of water, and the solution is added dropwise over the course of 30 minutes to 1464 ml of isopropyl acetate. The p-toluenesulphonic acid salt of 7-[2-(2-aminothiazol-4-yl)-2-(Z)-hydroximinoacetamido]-3-N,N-dimethylcarbamoyloxy-methyl-3-cephm4-carboxylic acid (isopropoxycarbonyloxy)ethylester crystallises. The suspension is stirred for a further 90 minutes whilst cooling with ice, and the crystals are filtered off through a suction filter, washed with a total of 225 ml of isopropyl acetate and dried in a vacuum for 17 hours at room temperature.

$^1$H-NMR as in example 1.

EXAMPLE 3

Production of the hydrochloric acid salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester by means of the toluenesulphonic acid salt of 7-[2-(2-aminothiazol-4-yl)-2-(Z)-hydroximinoacet amido]-3-N,N-dimethylcarbamoyl-oxymethyl-3-cephem-4-carboxylic acid (isopropoxycarbonyloxy) ethylester A solution of 8.65 kg of 7-amino-3-N,N-dimethylcarbamoyloxymethyl-3-cephem-4-carboxylic acid (isopropoxycarbonyloxy)ethylester in ca. 87 l of acetic acid isopropylester are mixed with 4.74 kg of N,O-bistrimethylsilylacetamide at a temperature of ca. –7°. Over the course of 30 minutes at ca. 0°, 5.59 kg of 2-(2-aminothiazol-4-yl)-2-(Z)-acetoxyiminoacetic acid chloride hydrochloride are added in 5 portions. A solution is always obtained again between the individual portions. After a further 50 minutes, the mixture is cooled to –12°, and 3.06 l of triethylamine are slowly added dropwise. The reaction mixture is allowed to flow slowly onto a mixture of 80 l of water, 20 l of isopropyl acetate and 20 l of saturated sodium bicarbonate solution. The phases are separated and the organic phase is re-extracted with 40 l of water. The pH of the aqueous phase is adjusted to 7.4 with saturated bicarbonate solution. The organic phase is cautiously concentrated by evaporation in a vacuum to ca. 40 l. 8 l of isopropanol and 6.1 kg of toluenesulphonic acid monohydrate are added to the residue, and the mixture is stirred for 2 hours at 35°. After 30 minutes the mixture is inoculated and crystallization of the p-toluenesulphonic acid salt of 7-[2-(2-aminothiazol-4-yl)-2-(Z)-hydroximinoacetamido]-3-N,N-dimethylcarbamoyloxy-methyl-3-cephem-4-carboxylic acid (isopropoxycarbonyloxy)-ethylester occurs. 120 l of acetic acid isopropylester are added dropwise to the suspension, and the reaction mixture is left to crystallise for a further 2 hours at a temperature of ca. 20°. The crystals are isolated, washed with a total of 50 l of isopropyl acetate and dried.

A mixture of 750 ml of isopropyl acetate and 150 ml of isopropanol is cooled to 5°. 30 g of the p-toluenesulphonic acid salt of 7-[2-(2-aminothiazol-4-yl)-2-(Z)-hydroximinoacetamido]-3-N,N-dimethyl-carbamoyloxy-methyl-3-cephem-4-carboxylic acid (isopropoxycarbonyloxy)ethylester, produced as described above, are added whilst stirring. 300 ml of ice-water are added. A solution is obtained. 35 ml of saturated bicarbonate solution are added, and the mixture is stirred for 10 minutes whilst cooling with ice. The pH value is adjusted to 5.3 with a little sodium bicarbonate. The phases are separated and the organic phase is washed back with 150 ml of water whilst cooling with ice. The pH value is re-adjusted to 5.9 with a little saturated sodium bicarbonate solution. The phases are separated and the organic phase is mixed with a mixture of 30 ml of isopropanol and 5.7 ml of 8N HCl. The solution is concentrated by evaporation to a total weight of ca. 150 g. The residue of evaporation is added dropwise over the course of 30 minutes to 1200 ml of vigorously stirred isopropyl acetate. The resultant suspension is stirred for another 30 minutes whilst cooling with ice, and the hydrochloric acid salt of 7-[2-(2-aminothiazol-4-yl)-2-(Z)-hydroximinoacetamido]-3-N,N-dimethylcarbamoyloxy-methyl-3-cephm4-carboxylic acid (isopropoxycarbonyloxy)ethylester is isolated, washed with a total of 150 ml of isopropyl acetate, and dried overnight.

$^1$HNMR: as in EP 0 484 966.

Comparison Example

Production of the hydrochloric acid salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester without intermediate isolation of the p-toluenesulphonic acid salt of 7-[2-(2-aminothiazol-4-yl)-2-(Z)-hydroximinoacetamido]-3-N,N-dimethylcarbamoyloxymethyl-3-cephem-4-carboxylic acid (isopropoxycarbonyloxy)ethylester A solution of 8.63 g of 7-amino-3-N,N-dimethylcarbamoyloxymethyl-3-cephm4-carboxylic acid (isopropoxycarbonyloxy)ethylester in ca. 73 ml of acetic acid isopropylester is cooled to 0° and mixed with 5.6 ml of N,O-bistrimethylsilylacetamide. At the same temperature, 5.7 g of 2-(2-aminothiazol4-yl)-2-(Z)-acetoxyiminoacetic acid chloride hydrochloride are added in small portions over the course of ca. 25 minutes. A solution is always produced again in the interim. The reaction mixture is cooled to –10° to –12°. 3 ml of triethylamine are added dropwise over the course of 20 minutes, and the resulting suspension is added dropwise over the course of 20 minutes, whilst cooling with ice, to a mixture of 72 ml of water, 23 ml of isopropyl acetate and 23 ml of saturated sodium bicarbonate solution. The phases are separated and the organic phase is re-extracted with 36 ml of water. The pH value of the aqueous phase is adjusted to pH 7.3 with sodium bicarbonate. The organic phase is mixed, in succession, with 40 ml of isopropanol, 14 ml of water and 1.8 ml of concentrated sulphuric acid. The mixture is stirred for 4 hours at room temperature and placed in a refrigerator over night. The solution is diluted with 20 ml of isopropyl acetate. 100 ml of water are added, and the pH of the mixture is adjusted to 5.28 with 2N NaOH. The phases are separated, the organic phase is re-extracted with 50 ml of water and the pH is carefully adjusted to 5.27 with 2 N NaOH, the phases are again separated, and subsequently the organic phase is cautiously concentrated by evaporation. The residue is dissolved in a mixture of 31 ml of acetic acid isopropyl ester, 9 ml of isopropanol and 1.7 ml of concentrated hydrochloric acid. The solution is added to 620 ml of acetic acid isopropyl ester over the course of 20 minutes under stirring. The precipitation is stirred for another one hour in an ice bath, and the hydrochloric acid salt of 7-[2-(2-aminothiazol-4-yl)-2-(Z)-hydroximinoacetamido]-3-N,N-dimethylcarbamoyloxy-methyl-3-cephem-4-carboxylic acid (isopropoxycarbonyloxy)-ethylester is isolated, washed with a total of 93 ml of isopropyl acetate and dried.

Monitoring the purity of the end product (hydrochloride) is effected by HPLC:

Process without isolation of the tosylate (comparison example): 4.17% by-products Process with isolation of the tosylate (example 3): 0.96% by-products

What we claim is:

1. A process for the production of a salt of 7-[2-(2-aminothiazol4-yl)-2-(Z)-hydroximinoacetamido]-3-N,N-dimethylcarbamoyloxymethyl-3-cephem-4-carboxylic acid (isopropoxycarbonyloxy)ethylester which comprises converting a p-toluene-sulphonic acid salt of 7-[2-(2-aminothiazol4-yl)-2-(Z)-hydroximinoacetamido]-3-N,N-dimethylcarbamoyloxymethyl-3-cephem-carboxylic acid (isopropoxycarbonyloxy)ethylester into a different salt with of 7-[2-(2-aminothiazol-4-yl)-2-(Z)-hydroximinoacetamido]-3-N,N-dimethylcarbamoyloxymethyl-3-cephem-carboxylic acid (isopropoxycarbonyloxy)ethylester.

2. A process according to claim 1 wherein the different salt is a hydrochloride salt.

3. A process of claim 1 wherein the p-toluene-sulfonic acid salt of 7-[2-(2-aminothiazol-4-yl)-2-(Z)-hydroximinoacetamido]-3-N, N-dimethylcarbamoyloxymethyl-3-cephem-carboxylic acid (isopropoxycarbonyloxy)ethylester is crystalline.

4. A process of claim 3 wherein the p-toluene-sulfonic acid salt of 7-[2-(2-aminothiazol-4-yl)-2-(Z)-hydroximinoacetamido]-3-N,N-dimethylcarbamoyloxymethyl-3-cephem-carboxylic acid (isopropoxycarbonyloxy)ethylester has at least the following d-values (Å) in the X-ray data: 28.247; 9.473; 5.014; 4.942; 3.994.

5. A pharmaceutical composition comprising a carrier and, as active ingredient, a p-toluene-sulfonic acid salt of 7-[2-(2-aminothiazol-4-yl)-2-(Z)-hydroximino-acetamido]-3-N,N-dimethylcarbamoyloxymethyl-3-cephem-carboxylic acid (isopropoxycarbonyloxy)ethylester.

\* \* \* \* \*